(12) United States Patent (10) Patent No.: US 12,650,388 B2

Tam et al. (45) Date of Patent: Jun. 9, 2026

(54) GEMSTONE TESTING DEVICE

(71) Applicant: Jubilee Diamond Instrument (s) Pte. Ltd., Singapore (SG)

(72) Inventors: Kui Lim Tam, Singapore (SG); Chuo Ann Ling, Central Link (SG)

(73) Assignee: Jubilee Diamond Instrument (S) Pte. Ltd., Singapore (SG)

( * ) Notice: Subject to any disclaimer, the term of this patent is extended or adjusted under 35 U.S.C. 154(b) by 137 days.

(21) Appl. No.: 18/579,486

(22) PCT Filed: Aug. 27, 2021

(86) PCT No.: PCT/SG2021/050515

§ 371 (c)(1),
(2) Date: Jan. 15, 2024

(87) PCT Pub. No.: WO2023/027626

PCT Pub. Date: Mar. 2, 2023

(65) Prior Publication Data

US 2024/0337601 A1      Oct. 10, 2024

(51) Int. Cl.

| | |
|---|---|
| *G01N 21/87* | (2006.01) |
| *G01N 21/64* | (2006.01) |
| *G01N 33/00* | (2006.01) |

(52) U.S. Cl.

CPC ......... *G01N 21/87* (2013.01); *G01N 21/6456* (2013.01); *G01N 33/389* (2024.05);
(Continued)

(58) Field of Classification Search

CPC .. G01N 21/87; G01N 21/6456; G01N 33/389; G01N 2021/6423; G01N 2021/6482

See application file for complete search history.

(56) References Cited

U.S. PATENT DOCUMENTS

| | | | | |
|---|---|---|---|---|
| 6,020,954 A | * | 2/2000 | Aggarwal | G01N 21/87 356/30 |
| 2005/0190357 A1 | * | 9/2005 | Sasian | G01N 21/8806 356/30 |

(Continued)

FOREIGN PATENT DOCUMENTS

| | | |
|---|---|---|
| WO | 2018115889 A1 | 6/2018 |
| WO | 2019123383 A1 | 6/2019 |
| WO | 2023027626 A1 | 3/2023 |

OTHER PUBLICATIONS

International Search Report and Written Opinion of the International Searching Authority in related International Application No. PCT/SG2021/050515, dated May 24, 2022, 10 pages.

*Primary Examiner* — Sang H Nguyen

(74) *Attorney, Agent, or Firm* — Thompson Patent Law Offices PC

(57) ABSTRACT

The application provides an improved gemstone testing device for testing a gemstone specimen. The device includes a housing, a platform for supporting the gemstone, a first light source for illuminating the gemstone, a second light source for exciting the gemstone, a third light source for exciting the gemstone, a light filter, a sheet of light absorptive material for absorbing blue light ray, a camera module for taking a picture of the gemstone, and a display module for displaying the picture and a corresponding reference picture of the gemstone to a user.

20 Claims, 5 Drawing Sheets

FIG. 1

(52) U.S. Cl.
     CPC ................ *G01N 2021/6423* (2013.01); *G01N*
                                    *2021/6482* (2013.01)

(56)                    References Cited

U.S. PATENT DOCUMENTS

| | | | |
|---|---|---|---|
| 2011/0181715 A1* | 7/2011 | Eales ................. | G01B 11/2433 |
| | | | 348/135 |
| 2013/0223046 A1* | 8/2013 | Bock ........................ | G02B 5/32 |
| | | | 362/125 |
| 2014/0139608 A1* | 5/2014 | Rosario ............... | B23K 26/359 |
| | | | 347/225 |
| 2015/0022801 A1 | 1/2015 | Lapa et al. | |
| 2016/0178530 A1* | 6/2016 | Davies ................... | G01N 21/64 |
| | | | 209/579 |
| 2020/0400646 A1* | 12/2020 | Tam ................... | G01N 21/8806 |
| 2021/0389247 A1* | 12/2021 | Tsai ................... | G02B 27/1013 |
| 2022/0155236 A1* | 5/2022 | Leizerson .............. | G01N 21/87 |
| 2022/0178835 A1* | 6/2022 | Lorenzi ................. | G01N 21/87 |
| 2022/0244189 A1* | 8/2022 | Rosenzweig .......... | G01N 21/87 |

* cited by examiner

GEMSTONE TESTING DEVICE

CROSS-REFERENCE TO RELATED APPLICATIONS

This application is a national stage application and claims the benefit of PCT Application Serial No. PCT/SG2021/050515, titled "Gemstone Testing Device," filed by Kui Lim Tam, et al., on Aug. 27, 2021.

TECHNICAL FIELD

The application relates to a device for testing gemstones, such as diamond simulants, earth-mined diamonds, and synthetic diamonds.

BACKGROUND

The diamond includes a native crystalline carbon that is very hard. The diamond can have a color or be colorless. When the diamond is transparent and free from flaws, it is highly valued as jewelry.

The earth-mined diamonds are obtained from the carbon being subjected to extreme heat and pressure deep underneath the earth's crust.

Synthetic diamonds are formed by a manufacturing or lab-grown process. Two methods are used to make synthetic diamond: the chemical vapor deposition (CVD) process and the high-pressure and high-temperature (HPHT) process. Synthetic diamonds produced from both methods possess similar chemical and physical properties as earth-mined diamonds.

The diamond simulant is a material that has Gemological characteristics that imitate earth-mined diamond. Cubic zirconia (CZ) is among the most common diamond simulant which is colorless and made of a cubic crystalline form of zirconium dioxide. Cubic zirconia does not carry the same properties as diamonds, and they do not produce brilliance and fire characteristics like diamonds.

SUMMARY

It is an objective of the application to provide an improved gemstone testing device.

The application provides a device for testing a gemstone.

The gemstone can refer to an earth-mined diamond, to a CVD (Chemical Vapor Deposition) diamond, to an HPHT (high pressure, high temperature) diamond, and to a diamond simulant, such as cubic zirconia, sapphire, and moissanite.

The device includes a housing, a gemstone platform, several light sources, at least one first light filter, at least one second light filter, a sheet of light absorptive material, a camera module, and a display module. The light sources comprise one or more first light sources, one or more second light sources, and one or more third light sources.

The housing is used for blocking external light rays from illuminating the gemstone.

The platform is placed inside the housing. It has an upper surface for supporting one or more gemstones, such as loose stones, rings, bracelets, earrings, and bangles.

The first light source provided a plurality of first light rays or white light rays to illuminate the gemstone. This allows a camera module to take a clear picture of the gemstone and any location marking near the gemstone.

The second light source produces a plurality of second light rays with a wavelength of about 365 nm. The second light rays are directed at the gemstone for exciting the gemstone such that the gemstone generates a first fluorescence emission.

Fluorescence refers to luminescence that is caused by the absorption of radiation at one wavelength by a gemstone. This is followed by nearly immediate reradiation usually at a different wavelength of the gemstone. The reradiation ceases almost at once when the incident radiation stops.

Phosphorescence refers to luminescence that is caused by the absorption of radiations, such as UV light. The luminescence continues for a noticeable time after these radiations have stopped.

Similarly, the third light source produces a plurality of third light rays with a wavelength of about 222 nm for exciting the gemstone to generate a second fluorescence emission and a phosphorescence emission.

The first light filter acts to allow the second light rays with a first predetermined range of wavelengths to excite the gemstone, the first predetermined range extending between about 350 nm and about 380 nm. In other words, the first light filter blocks or prevents the second light rays with wavelengths outside this range from reaching the gemstone.

Similarly, the second light filter acts to allow the third light rays with a second predetermined range of wavelengths to excite the gemstone, the second predetermined range extending between about 210 nm and about 230 nm. Put differently, the second light filter blocks or prevents the third light rays with wavelengths outside this range from reaching the gemstone.

The sheet of light absorptive material is placed on the top surface of the platform. It acts to absorbs blue light rays. In effect, the second or the third light source can produce blue light rays. The light absorptive material sheet absorbs the blue light rays, thereby preventing any reflected blue light rays from reaching the gemstone.

The light absorptive material sheet is provided with one or more location markings for identifying the location of the gemstone that is placed near the location marking.

The camera module is used for taking a picture of the respective fluorescence emission and a picture of the respective phosphorescence emission of the gemstone.

The display module displays the picture of the fluorescence emission or the phosphorescence emission of the gemstone as well as corresponding reference pictures of the gemstone. This allows the user to identify the type of gemstone.

This device allows a fast and simple, and inexpensive way of identifying or classification of the gemstone.

The first light source is often adapted to emit white light rays for illuminating the gemstone, thereby allowing the camera module to take a clear picture of the gemstone with any location marking.

In one implementation, the platform includes a flat tray for supporting the gemstone.

In another implementation, the platform includes a velvet box for supporting the gemstone.

A piece of white paper can be placed on top of the platform. The white paper often does not include an optical brightening agent.

This prevents specific wavelengths of light rays been reflected from the white paper, such as blue light rays. The reflected light rays can affect the fluorescence emission picture of the gemstone. The white paper can also diffuse light rays, which are directed toward the white paper to illuminate it. In other words, the white paper scatters these light rays in different directions.

The camera module can be provided as a part of a mobile phone to save cost.

The display module can include a capacitive touch screen.

BRIEF DESCRIPTION OF THE DRAWINGS

The subject matter of the application is described in greater detail in the accompanying Figures, in which.

DETAILED DESCRIPTION OF ILLUSTRATIVE EMBODIMENTS

In the following description, details are provided to describe the embodiments of the specification. It shall be apparent to one skilled in the art, however, that the embodiments may be practiced without such details.

Some parts of the embodiments have similar parts. The similar parts may have the same names or similar part numbers with an alphabet symbol or prime symbol. The description of one part applies by reference to another similar part, where appropriate, thereby reducing the repetition of text without limiting the disclosure.

Figure 1:
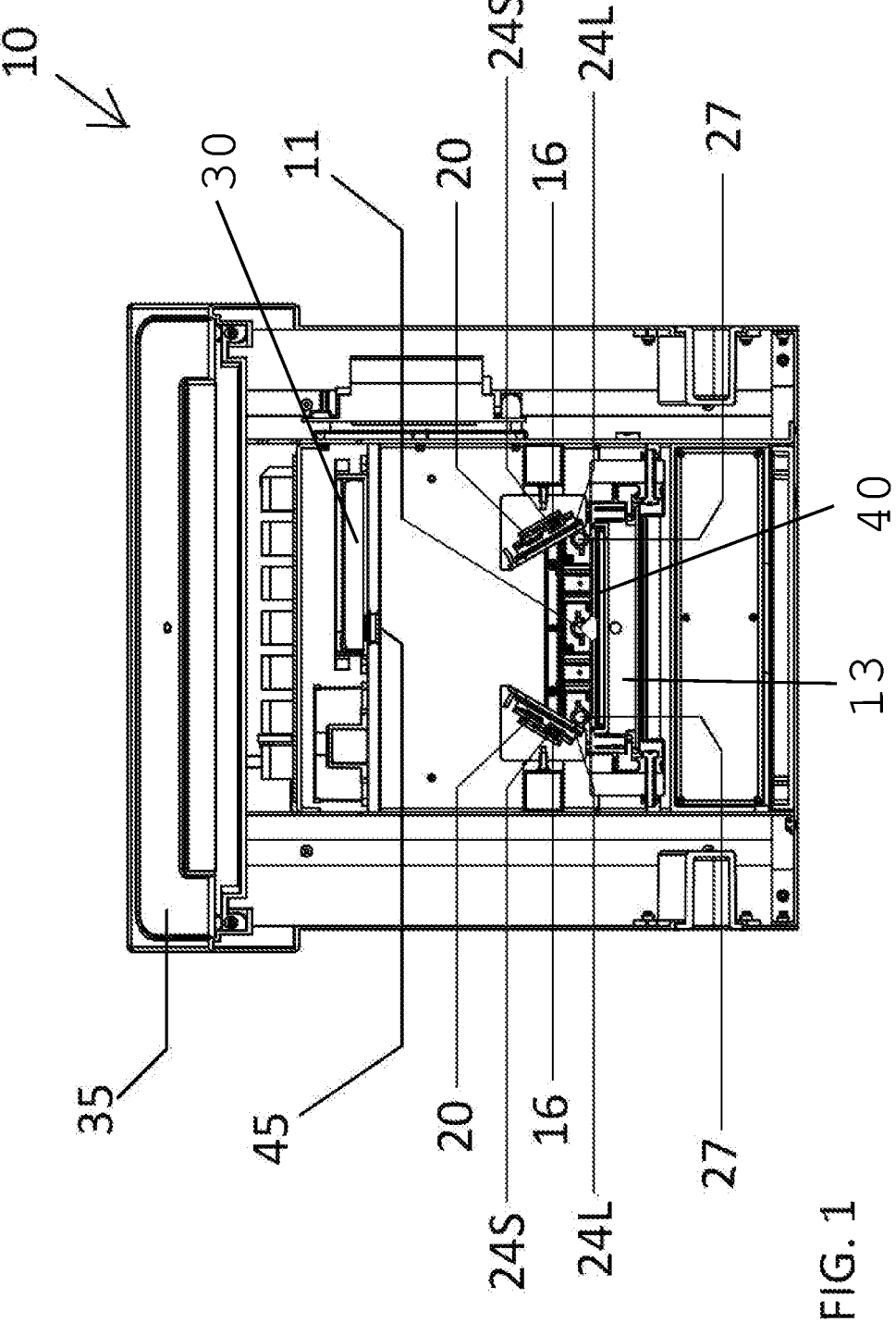
FIG. 1 illustrates an internal view of an improved gemstone testing instrument.

FIG. 1 shows an improved instrument 10 for testing gemstones 11.

This instrument 10 includes a flat tray 13, one two longwave light module, one two shortwave light module, two UV (ultraviolet) filters 24L with two UV filters 24S, white LEDs 27, a handphone 30, and a housing 35.

In detail, the longwave light module includes at least two longwave light sources 16. Each/All of the longwave light sources 16 is/are placed on a piece of printed circuit board. One longwave light source 16 is placed on one side of the gemstone 11 while another longwave light source 16 is placed on another side of the gemstone 11. The UV filters 24S are placed next to the respective longwave light sources 16.

Similarly, one shortwave light module includes two shortwave light sources 20. Each shortwave light source 20 is placed on a piece of printed circuit board. One shortwave light source 20 is placed on one side of the gemstone 11 while another shortwave light source 20 is placed on another side of the gemstone 11. The UV filters 24L are placed next to the respective shortwave light sources 20.

Figure 3:
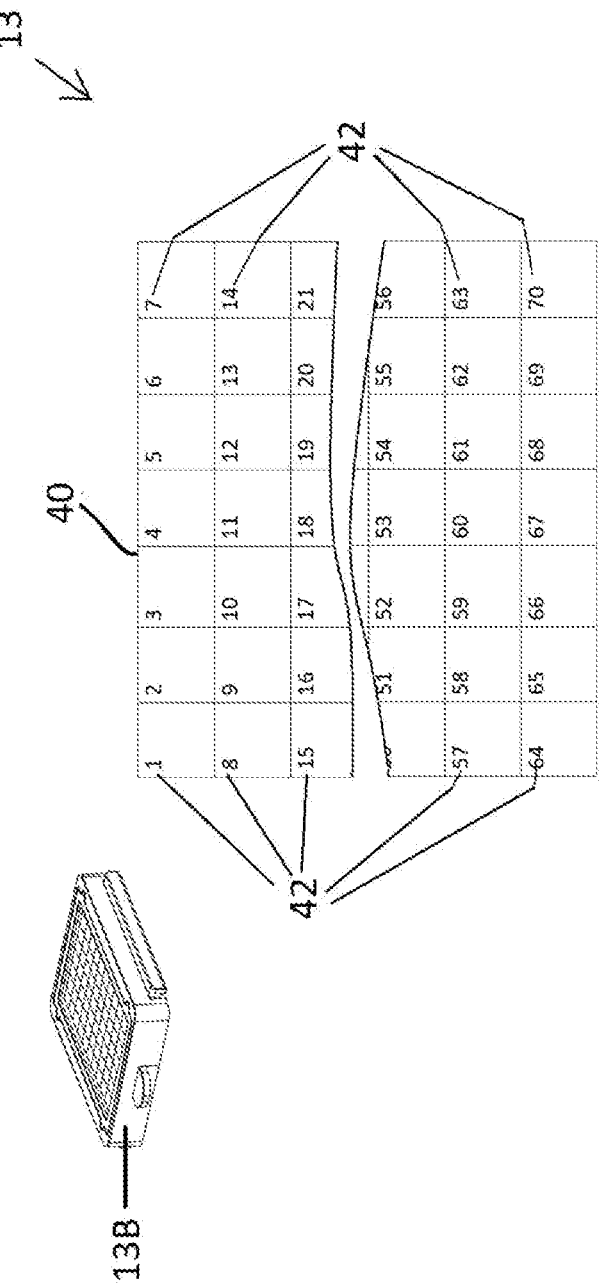
FIG. 3 illustrates location markings of a tray of the gemstone testing instrument of FIG. 1.

The flat tray 13 includes a sheet 40 of light absorptive material being placed on the top surface of the flat tray 13. This sheet 40 includes several gemstone location markings 42, as shown in FIG. 3.

Figure 5:
FIG. 5 illustrates parts of a handphone for the gemstone testing instrument of FIG. 1.
Figure 5:
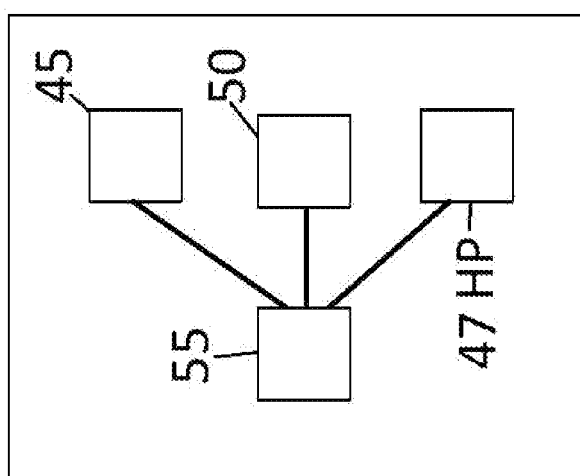

The handphone 30 includes a camera module 45. As an illustrative example shown in FIG. 5, the handphone may also include a USB (Universal Serial Port) port 47HP, a storage module 50, and a GPU (Graphics Processing Unit) module 55. The storage module 50 can include a RAM (Random Access Memory) unit and a flash memory unit. The flash memory unit refers to an electronic non-volatile memory storage medium.

The housing 35 includes a capacitive touch screen 57.

The housing 35 encloses the flat tray 13, the longwave light sources 16, the shortwave light sources 20, the UV filters 24L and 24S, the white LEDs 27, and the handphone 30.

In a general sense, the flat tray 13 can be provided by a rectangular velvet box.

Functionally, the instrument 10 is used to test a gemstone using fluorescence emission and phosphorescence emission of the gemstone.

Fluorescence refers to luminescence that is caused by the absorption of radiation at one wavelength by a gemstone. This is followed by nearly immediate reradiation usually at a different wavelength of the gemstone. The reradiation ceases almost at once when the incident radiation stops.

Phosphorescence refers to luminescence that is caused by the absorption of radiations, such as UV light. The luminescence continues for a noticeable time after these radiations have stopped.

The gemstone can refer to an earth-mined diamond, a CVD (Chemical Vapor Deposition) diamond, an HPHT (high pressure, high temperature) diamond, and a diamond simulant, such as cubic zirconia, sapphire, and moissanite.

The HPHT diamond is produced in a laboratory, and it is subjected to high pressure and high temperature which mimics growth conditions for natural diamond.

The CVD diamond refers to an artificial diamond that is produced using a chemical vapor deposition crystal formation process.

Cubic zirconia (CZ) is among the most common diamond simulants, which are colorless and made of a cubic crystalline form of zirconium dioxide. CZ does not carry the same properties as diamonds, and they do not produce brilliance and fire-like colors as diamonds do. However, CZ is visually like the diamonds, and it has a low cost.

Referring to the flat tray 13, it is used to carry loose gemstones. The tray 13 can also be used as a platform to carry jewelry such as rings, earrings, bangles, bracelets, and necklaces.

The jewelry can be tucked in tray 13 or rest on tray 13 so that gemstones of the jewelry are facing upward for being exposed to UV light rays for excitation. The rings, earrings, and bangles are often tucked in tray 13 while the bracelets and necklaces are often resting on tray 13.

Figure 2:
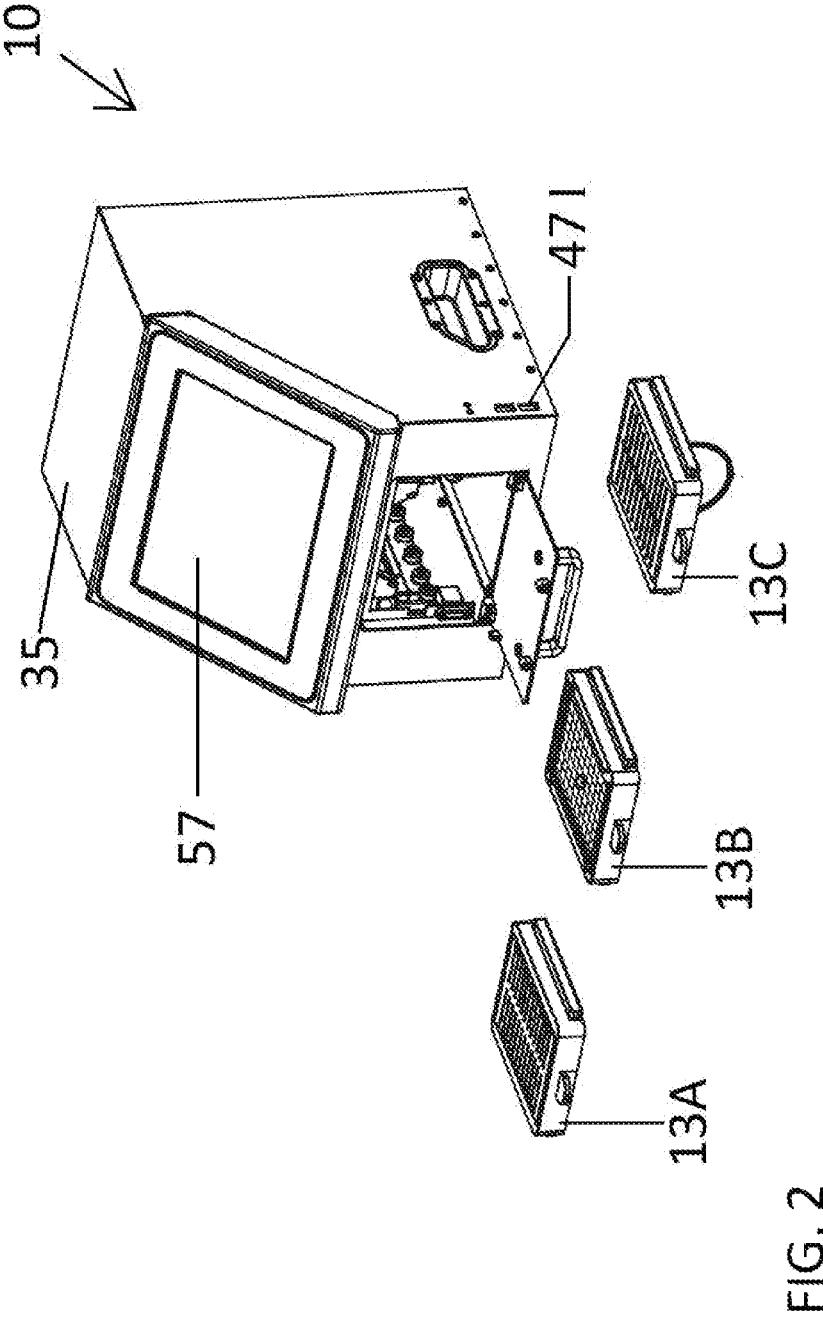
FIG. 2 illustrates an external view of the gemstone testing instrument of FIG. 1.
Figure 4:
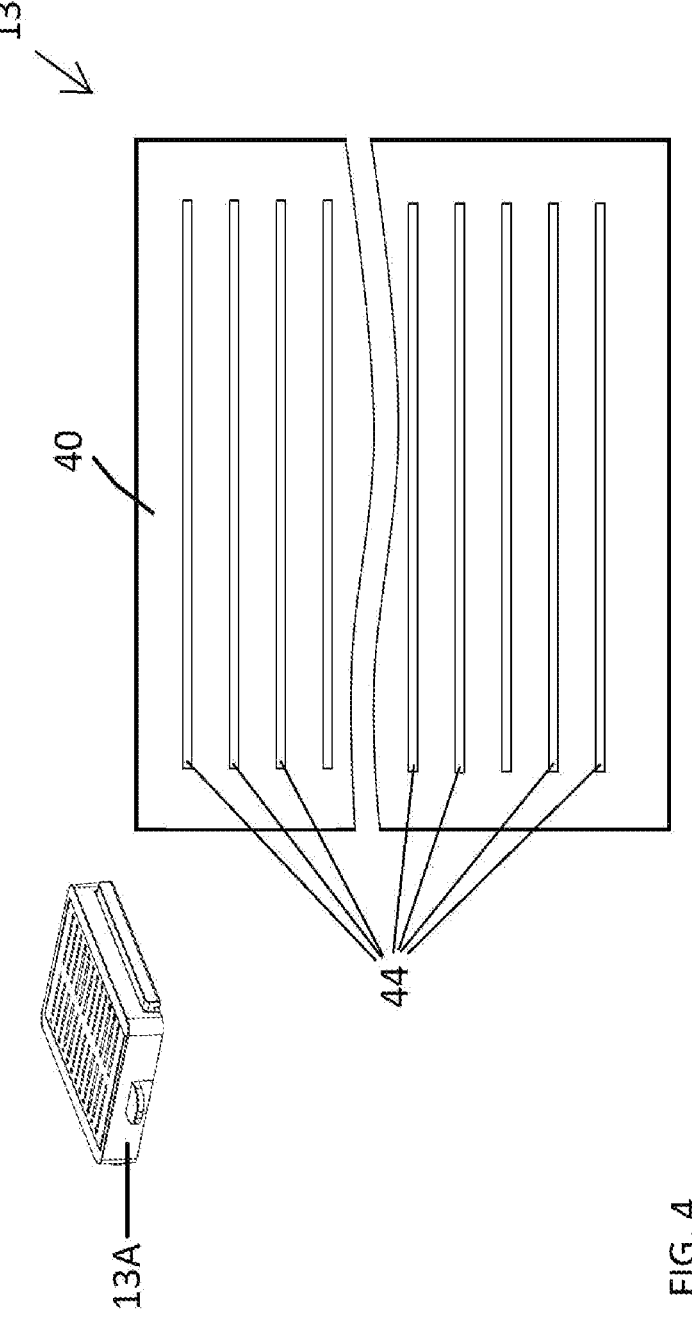
FIG. 4 illustrates a tray of the gemstone testing instrument of FIG. 1, which is adapted for receiving a piece of jewelry.

FIG. 4 shows a tray 13 which includes rows 44 that is adapted for jewelry. The jewelry can be tucked into one of the rows 44. FIG. 2 shows instrument 10 with a flat tray 13A that is adapted for carrying rings, a flat tray 13B that is adapted for carrying loose gemstones, and a flat tray 13C that is adapted for carrying bangles.

In detail, the gemstone is intended for placing on the light absorptive material sheet 40 of tray 13 such that the gemstone is placed near a location marking 42 of the light absorptive material sheet 40 for easily identifying the location of the gemstone.

The light absorptive material sheet 40 absorbs blue light rays that originate from a UV light source.

In one implementation, the light absorptive material sheet 40 is provided as a sheet of yellow material, such as a sheet of sponge or a piece of yellow cloth.

In another implementation, the light absorptive material sheet 40 is provided as a white paper that does not include an optical brightening agent (OBA). The OBA refers to an additive that is used to enhance the whitening effects or appearance of the paper. The additive comprises chemical compounds to absorb ultraviolet light rays and then emit light rays in the blue region, typically between 420 nm and 470 nm.

In effect, this OBA-free white paper does not produce any blue fluorescence when the paper is illuminated with UV light rays. The surface of the paper then appears as dull white. This allows the paper to enhance the visible color of the fluorescence emission of the gemstone and to improve the quality of the picture taken by the camera module 45.

In a further implementation, the light absorptive material sheet 40 is provided as a rough film.

In a general sense, the light absorptive material sheet 40 can include two sheets comprising a sheet of yellow material and a sheet of yellow transparent plastic.

The white paper could have numbering so that the location of the gemstones can be known easily. It is suitable to put the loose stones on the white paper where the loose stones can rest on the paper with a pavilion or table facing downwards. The OBA-free white paper is probably optional to be used on the platform.

Referring to the longwave light source 16, it produces longwave light rays with a wavelength of about 365 nm. The longwave light rays are a form of UV light rays or longwave UV radiation.

The total power radiant of the longwave light rays is sufficiently high to excite the gemstone to produce fluorescence emission.

In this embodiment, the gemstone absorbs light rays or other electromagnetic radiation, such as UV or X-ray radiation. Shortly after this, the gemstone emits visible light rays. Typically, the emitted light rays have a longer wavelength or lower energy than the wavelength or energy of the absorbed radiation or excitation radiation.

Referring to the shortwave light source 20, it produces shortwave light rays with a wavelength of about 222 nm. The shortwave light rays are a form of UV light rays or shortwave UV radiation.

The total power radiant of the shortwave light rays is sufficiently high to excite the gemstone to produce fluorescence or phosphorescence emission.

Referring to the light absorptive material sheet 40, it absorbs any blue light rays that are originated from the shortwave light source 20 or the longwave light source 16. This allows the camera module 45 to take a more accurate image of the fluorescence color that is emitted from the gemstone, thereby allowing the gemstone to be differentiated easily.

Referring to the UV filter 24S, it is used to filter the longwave light rays of the longwave light source 16.

The UV filter 24S allows a specific range of the wavelengths of the longwave light rays to pass through the filter 24S while blocking light rays outside this range from passing through the UV filter 24S. In other words, the UV filter 24S acts as a wavelength bandpass filter.

Several implementations of the filter 24S are possible. In one implementation, the filtered longwave light rays have wavelengths ranging from about 350 nm to about 380 nm. In another implementation, the filtered longwave light rays have wavelengths ranging from about 360 nm to about 370 nm. In a further implementation, the filtered longwave light rays have wavelengths ranging from about 315 nm to about 400 nm.

These filtered longwave light rays serve as excitation radiation to distinguish the earth-mined diamonds from synthetic diamonds and simulants.

The longwave light rays advantageously cause the gemstone to emit light with a uniform fluorescence color or emission for easy identification of the gemstone.

When the earth-mined diamonds, apart from type IIa diamonds, are exposed to the longwave light rays, they emit a certain shade of blue, bluish-white, or yellowish-white fluorescence instantly. These fluorescence colors are due to the nitrogen-related defects that exist naturally in earth-mined diamonds.

The type IIa diamonds are either extracted or mined from the ground or are produced in the laboratory. The type IIa diamonds exhibit no measurable traces of nitrogen or boron in their structure. The type IIa diamonds might not show these fluorescence colors because they generally lack nitrogen defects in their crystal lattice.

Similarly, referring to the UV filter 24L, it is used to filter the shortwave light rays of the shortwave light source 20.

The UV filter 24L allows a specific range of the wavelengths of the shortwave light rays to pass through the filter 24L while blocking light rays outside this range from passing through the UV filter 24L. In short, the UV filter 24L acts as a bandpass filter.

Several implementations of the filter 24L are possible.

In one implementation, the filtered shortwave light rays have wavelengths ranging from about 210 nm to about 230 nm. In another implementation, the filtered shortwave light rays have wavelengths ranging from about 210 nm to about 240 nm. In yet another implementation, the filtered shortwave light rays have wavelengths ranging from about 200 nm to about 280 nm.

These filtered shortwave light rays serve as excitation radiation to distinguish the CVD and HPHT diamonds from other gemstones.

The filtered light shortwave rays advantageously cause the gemstone to emit light with a uniform fluorescence or phosphorescence emission for easy identification of the gemstone.

When the CVD diamonds are exposed to the shortwave light rays, they emit red, orange-red, yellow, or bright green fluorescence.

When the HPHT diamonds are exposed to the shortwave light rays, they can emit green fluorescence. The HPHT diamonds can also produce greenish-blue or white phosphorescence emission after about the shortwave light rays are turned off, and the phosphorescence emission can last from 5 seconds to 30 seconds.

Referring to the white LEDs 27, they are used to provide sufficient light to the gemstones or jewelry in the enclosed housing 35 so that the camera module 45 can clearly view the gemstones or jewelry on the tray 13 together with its location markings 42. Under this bright light, the camera module 45 can take clear pictures of all gemstones or jewelry for storing these pictures in the storage module 50 of the camera module 45.

Referring to the camera module 45, it is used to take pictures of the gemstones.

Loose gemstones are intended for placing on with their tables or major surfaces facing downwards.

The gemstones can be placed in different states.

In a first state, the white LEDs 27 are activated to provide a bright environment for the gemstones while the longwave light sources 16 and the shortwave light sources 20 are not activated for exciting the gemstones. The camera module 45 can then take pictures of the gemstones that are placed on the flat tray 13, together with the location markings 42 that are located next to the corresponding gemstones.

In a second state, the white LEDs 27, and the shortwave light sources 20 are not activated while the longwave light sources 16 are activated to produce light rays for exciting the gemstone to produce fluorescence emission. During the emission, the camera module 45 captures pictures of the fluorescence emission of the respective gemstone.

In a third state, the white LEDs 27, and the longwave light sources 16 are not activated while the shortwave light sources 20 are activated to produce light rays for exciting the gemstone to produce fluorescence or phosphorescence emission. During the emission, the camera module 45 captures corresponding pictures of the fluorescence or phosphorescence emission of the gemstone.

It should be noted that, in these states, the white LEDs 27 do not generate any light rays that can interfere with the longwave light rays nor with the shortwave light rays.

Referring to the storage module 50, it is used for saving or storing pictures of the gemstone.

The storage module 50 of the camera module 45 can include an SD (Secure Digital) card. When the storage space of the card is full, the user can transfer the picture file to a removable storage device, such as a removable disk.

Referring to the capacitive touch screen 57, it is used to display a graphic unit interface (GUI) that allows a user to use a stylus, a finger, or a mouse to select the desired gemstone to analyze the gemstone.

The screen then displays pictures of the fluorescence and phosphorescence emission of the desired gemstone.

Furthermore, the screen can also display reference colors of different types of gemstones, thereby allowing the user to compare the emission of the tested gemstones with the reference colors.

Referring to the USB port 47HP of the handphone 30, it enables the saved pictures in the storage module 50 to be transferred to an external data storage device, such as a flash drive that is plug into the USB port 47I of the instrument 10.

In a general sense, the flash drive can be replaced with an electronic board.

In a general sense, the handphone 30 can be replaced by a computing microprocessor.

In a special embodiment, the instrument 10 is provided with object recognition processing.

The object recognition software is used to detect the location of the loose gemstones on the tray 13. The software can use circle detection analysis using computer vision or machine vision algorithms.

The storage module 50 is sized for storing a predetermined of pictures and the GPU module 55 has sufficient processing power to perform object recognition processing.

The handphone 30 can be used to pictures of the gemstones on the tray 13 for easier identification of the location of the gemstones.

When the camera module 45 is positioned above the gemstones, a picture taken by the camera module 45 would show the loose gemstones as having a round shape. This enables an algorithm to recognize the round shape and to identify the location of the gemstones accurately.

The color detection and analysis are done through software programming tools, such as C programming and Python programming language. The saved pictures are analyzed by measuring the percentage of primary colors (red, blue, and green) on each pixel. The gemstone's colors comprise blue, bluish-white, red, green, yellow, orange-red, and greenish-blue. If the colors of the pixels fall within a predetermined range, the gemstone will be classified accordingly, such as earth-mined diamonds, CVD diamonds, HPHT diamonds, or diamond simulants.

In one embodiment, the tray 13 could accommodate about 70 small-sized loose gemstones or about 40 big-sized loose gemstones.

The total power radiant of the longwave light rays ranges from about 1 watt (W) to about 10 W. Similarly, the total power radiant of the shortwave light rays ranges from about 10 W to about 25 W.

In a variant of the embodiment, the total power radiant of the shortwave light rays ranges from about 1 W to about 10 W.

The camera module 45 has a high sensitivity to take photographs in very low light intensity of up to 0.001 lux. The resolution of the camera module 45 ranges from 2 MP (megapixels) to 13 MP.

The size of the capacitive touch screen 57 is about 7 inches to about 10 inches, which allows a clear display of the color emission of the gemstones.

A method of testing a gemstone is described below.

The method includes a step of placing a loose gemstone on the flat tray 13.

The loose gemstone can be replaced by a ring or bangle.

Electrical power is then connected to the instrument 10. After this, the instrument 10 is allowed to warm up and load software for a predetermined period.

The flat tray 13 with the gemstone is afterward placed inside the housing 35.

A user then touched or pressed a "preview" button on the touch screen 57 to switch on the white LEDs 27 and later takes a picture of the gemstone on the flat tray 13.

A "quit" button on the touch screen 57 is pressed if the picture is not in focus and is not clear. Following this, the white LEDs 27 are switched off.

The user later presses a "start test" button on the touch screen 57 to energize the longwave light source 16 while not energizing the shortwave light source 20.

The camera module 45 then takes a photograph of fluorescence emission of the gemstone while the longwave light source 16 is exciting the gemstone.

Similarly, the user also presses a "start test" button on the touch screen 57 to energize the shortwave light source 20 while not energizing the longwave light source 16. The camera module 45 takes a photograph of the gemstone of fluorescence emission of the gemstone while the shortwave light source 20 is exciting the gemstone and it takes a photograph of a phosphorescence emission of the gemstone when the shortwave light source 20 is turned off.

Four pictures of the gemstone are then displayed on the screen.

The first picture shows the gemstone when the gemstone is subjected to light rays from the white LEDs 27.

The second picture shows fluorescence emission of the gemstone when the gemstone is subjected to the longwave light rays with a longwave wavelength of about 365 nm.

The third picture shows fluorescence emission of the gemstone when the gemstone is subjected to the shortwave light rays with a shortwave wavelength of about 222 nm.

The fourth picture shows phosphorescence emission of the gemstone immediately after the shortwave light rays are turned off, after subjecting the gemstone with the shortwave light rays for a predetermined of about 4 seconds.

The user then selects the fluorescence and the phosphorescence pictures to compare with corresponding reference pictures to determine the classification or type of the gemstone.

The user may press a "Zoom" button on the touch screen 57 to select a region of the picture and clicking the mouse to enlarge the selected region.

After this, the user presses a "transfer file" button of the touch screen 57 to transfer pictures saved in the handphone 30 or a microprocessor to a flash drive of the instrument 10 for safekeeping. To do this, the flash drive can be connected to a USB data port 47I of the instrument 10.

Manual comparison with the reference pictures allows this method to be fast and simple, wherein the light intensities and colors of the pictures of the gemstones are compared with a reference table for each diamond type.

If an automated means is used in place of manual comparison, the picture of the gemstone would be converted into several areas with different light intensities and different colors according to 8 bits of color analyses. This process requires the storage module 50 to have a higher capacity to run the color analyses precisely.

In another embodiment, the shortwave light source 20 is adapted to produce light rays with a wavelength of about 254 nm. The light rays with a wavelength of about 254 nm provide another means of exciting the gemstone.

Although the above description contains many specificities, these should not be construed as limiting the scope of the embodiments but merely providing an illustration of the foreseeable embodiments. Especially the above-stated advantages of the embodiments should not be construed as limiting the scope of the embodiments but merely to explain possible achievements if the described embodiments are put into practice. Thus, the scope of the embodiments should be determined by the claims and their equivalents, rather than by the examples that are given.

REFERENCE NUMBERS 10 instrument
11 gemstone
13 flat tray
13A flat tray
13B flat tray
13C flat tray
16 longwave light source
20 shortwave light source
24L UV filter
24S UV filter
27 white LEDs
30 handphone
35 housing
40 sheet of light absorptive material
42 location markings
44 row
45 camera module
47HP USB port
47I USB port
50 storage module
55 GPU module
57 touch screen

The invention claimed is:

1. A device for testing a gemstone, the device comprises:
a housing for blocking external light rays from illuminating the gemstone,
a platform with an upper surface being provided inside the housing for supporting the gemstone,
at least one first light source for providing a plurality of first light rays to illuminate the gemstone,
at least one second light source for producing a plurality of second light rays with a wavelength of about 365 nm for exciting the gemstone to generate a first fluorescence emission,
at least one third light source for producing a plurality of third light rays with a wavelength of about 222 nm for exciting the gemstone to generate a second fluorescence emission and a phosphorescence emission, at least one first light filter for allowing the second light rays with a first predetermined range of wavelengths to excite the gemstone, the first predetermined range extending between about 350 nm and about 380 nm,
at least one second light filter for allowing the third light rays with a second predetermined range of wavelengths to excite the gemstone, the second predetermined range extending between about 210 nm and about 230 nm,
a sheet of light absorptive material being provided on the upper surface of the platform for absorbing blue light rays,
wherein the light absorptive material sheet is provided as a sheet of yellow material and/or a dull white paper,
wherein at least one location marking is provided on the light absorptive material sheet,
a camera module for taking a picture of a fluorescence emission and a picture of a phosphorescence emission of the gemstone, and
a display module for displaying the picture and a corresponding reference picture of the gemstone to a user.

2. The device according to claim 1, wherein the at least one first light source emits white light rays.

3. The device according to claim 1, wherein the platform comprises a flat tray.

4. The device according to claim 1, wherein the platform comprises a velvet box.

5. The device according to claim 1, wherein the dull white paper is void of an optical brightening agent (OBA).

6. The device according to claim 1, wherein a mobile phone comprises the camera module.

7. The device according to claim 6, wherein the mobile phone comprises:
a storage module operably coupled to the camera module; and,
a GPU module operably coupled to the storage module, wherein the storage module is configured to store the picture captured by the camera module and the GPU module is configured to perform object recognition processing based on the picture stored in the storage module and an object recognition processing software stored in the storage module.

8. The device according to claim 1, wherein the display module comprises a capacitive touch screen.

9. The device according to claim 1, wherein:
at least one second light module comprises two second light sources, and
at least one third light module comprises two third light sources.

10. The device according to claim 1, wherein the camera module is configured to take photographs in a light intensity of 0.001 lux, and the camera module is configured to take the picture with a resolution ranges from 2 megapixels to 13 megapixels.

11. A device for testing a gemstone, the device comprises:
a housing for blocking external light rays from illuminating the gemstone,
a platform with an upper surface being provided inside the housing for supporting the gemstone,
at least one first light source for providing a plurality of first light rays to illuminate the gemstone,
at least one second light source for producing a plurality of second light rays with a wavelength of about 365 nm for exciting the gemstone to generate a first fluorescence emission,
at least one third light source for producing a plurality of third light rays with a wavelength of about 222 nm for exciting the gemstone to generate a second fluorescence emission and a phosphorescence emission, at least one first light filter for allowing the second light rays with a first predetermined range of wavelengths to excite the gemstone, the first predetermined range extending between about 350 nm and about 380 nm, at least one second light filter for allowing the third light rays with a second predetermined range of wavelengths to excite the gemstone, the second predetermined range extending between about 210 nm and about 230 nm, a sheet of light absorptive material being provided on the upper surface of the platform for absorbing blue light rays, wherein the light absorptive material sheet is provided as a sheet of yellow material and/or a dull white paper, wherein the dull white paper is void of an optical brightening agent (OBA), wherein at least one location marking is provided on the light absorptive material sheet, a camera module for taking a picture of a fluorescence emission and a picture of a phosphorescence emission of the gemstone, wherein the camera module is embedded in a mobile phone, and a display module for displaying the picture and a corresponding reference picture of the gemstone to a user.

12. The device according to claim 11, wherein the first light source emits white light rays.

13. The device according to claim 11, wherein the platform comprises a flat tray.

14. The device according to claim 11, wherein the platform comprises a velvet box.

15. The device according to claim 11, wherein the display module comprises a capacitive touch screen.

16. The device according to claim 11, wherein at least one second light module comprises two second light sources, and at least one third light module comprises two third light sources.

17. The device according to claim 11, wherein the camera module is configured to take photographs in a light intensity of 0.001 lux, and the resolution of the camera module ranges from 2 megapixels to 13 megapixels.

18. The device according to claim 11, wherein the mobile phone comprises:

a storage module operably coupled to the camera module; and, a GPU module operably coupled to the storage module, wherein the storage module is configured to store the picture captured by the camera module and the GPU module is configured to perform object recognition processing based on the picture stored in the storage module and an object recognition processing software stored in the storage module.

19. The device according to claim 18, wherein the camera module is positioned above the platform such that, when a gemstone is loaded into the platform and the camera module takes the picture of the gemstone, the picture comprise a round shape corresponding to the gemstone, wherein the object recognition processing software is configured to identify the gemstone based on the round shape.

20. The device according to claim 11, wherein the picture is configured to be display on a graphic unit interface, such that a user is allowed to use a stylus, a finger, or a mouse to select any one of a gemstone supported by the platform and analyze the selected any one of the gemstone.

* * * * *